(12) United States Patent
Baker

(10) Patent No.: US 6,340,655 B1
(45) Date of Patent: Jan. 22, 2002

(54) HERBICIDAL EMULSIFIABLE CONCENTRATE COMPOSITIONS OF DINITROANILINE AND OXYACETAMIDE HERBICIDES

(75) Inventor: Ivor Philip Baker, Southampton (GB)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/595,246

(22) Filed: Jun. 15, 2000

Related U.S. Application Data

(60) Provisional application No. 60/140,229, filed on Jun. 22, 1999, now abandoned.

(51) Int. Cl.$^7$ .................. A01N 25/22; A01N 33/18; A01N 43/824
(52) U.S. Cl. .................. 504/139; 504/363; 504/364
(58) Field of Search .................. 504/139, 363, 504/364

(56) References Cited

U.S. PATENT DOCUMENTS

| | | | |
|---|---|---|---|
| 2,954,396 A | 9/1960 | Ayers et al. | 260/482 |
| 3,898,075 A | 8/1975 | Freud et al. | 71/111 |
| 4,408,055 A | 10/1983 | Förster et al. | 548/125 |
| 4,509,971 A | 4/1985 | Förster et al. | 71/90 |
| 4,540,430 A | 9/1985 | Förster et al. | 71/90 |
| 4,549,899 A | 10/1985 | Förster et al. | 71/90 |
| 4,585,471 A | 4/1986 | Förster et al. | 71/90 |
| 4,645,525 A | 2/1987 | Förster et al. | 71/88 |
| 4,756,741 A | 7/1988 | Förster et al. | 71/90 |
| 4,784,682 A | 11/1988 | Förster et al. | 71/88 |
| 4,788,291 A | 11/1988 | Förster et al. | 548/187 |
| 4,833,243 A | 5/1989 | Förster et al. | 540/480 |
| 4,968,342 A | 11/1990 | Förster et al. | 71/90 |
| 4,988,380 A | 1/1991 | Förster et al. | 71/90 |
| 5,090,991 A | 2/1992 | Förster et al. | 71/90 |
| 5,234,896 A | 8/1993 | Wagner et al. | 504/267 |
| 5,624,884 A * | 4/1997 | Morgan et al. | 504/148 |
| 5,759,955 A | 6/1998 | Santel et al. | 504/132 |
| 6,071,858 A * | 6/2000 | Modrcin et al. | 504/134 |

FOREIGN PATENT DOCUMENTS

| | | |
|---|---|---|
| DE | 197 20 367 A | 11/1997 |
| EP | 0 300-344 A1 | 7/1988 |
| EP | 0 500 934 A1 | 10/1989 |
| EP | 0 496 989 A | 8/1992 |
| WO | 94 02014 A | 2/1994 |
| WO | WO 97/08160 | 8/1995 |

* cited by examiner

*Primary Examiner*—S. Mark Clardy
(74) *Attorney, Agent, or Firm*—Barbara V. Maurer

(57) ABSTRACT

The present invention provides herbicidal emulsifiable concentrate compositions of dinitroaniline herbicides (e.g., pendimethalin) and oxyacetamide herbicides (e.g., fluthiamid). The compositions utilize phosphoric acid as a stabilizing agent to prevent degradation of the oxyacetamide herbicide component during storage.

19 Claims, No Drawings

HERBICIDAL EMULSIFIABLE CONCENTRATE COMPOSITIONS OF DINITROANILINE AND OXYACETAMIDE HERBICIDES

This application claims priority from provisional application(s) serial No. 60/140,229 filed on Jun. 22, 1999 abandoned.

BACKGROUND OF THE INVENTION

Dinitroaniline herbicides such as pendimethalin and trifluralin, and oxyacetamide herbicides such as fluthiamid are known in the art. Combination treatments using these types of herbicides are disclosed in U.S. Pat. Nos. 4,968,342 and 5,759,955; and in German Application No. 19720367. However, emulsifiable concentrate compositions comprising dinitroaniline and oxyacetamide herbicides are not known in the art.

U.S. Pat. No. 3,898,075 relates to stabilized liquid compositions containing m-biscarbamates and organic acids. U.S. Pat. No. 2,954,396 describes a method for stabilizing carbamate esters with certain hydrolysis inhibitors. However, neither U.S. Pat. No. 3,898,075 nor U.S. Pat. No. 2,954,396 describe any method for the stabilization of oxyacetamide herbicides.

It is therefore an object of the present invention to provide stable emulsifiable concentrate compositions of dinitroaniline herbicides and oxyacetamide herbicides.

Other objects and advantages of the present invention will be apparent to those skilled in the art from the description below and the appended claims.

SUMMARY OF THE INVENTION

The present invention relates to a herbicidal emulsifiable concentrate composition comprising, on a weight to weight basis, about 15% to 40% of a dinitroaniline herbicide, about 1% to 10% of an oxyacetamide herbicide, about 0.01% to 1% phosphoric acid, up to about 30% of an emulsifier or mixture of emulsifiers, up to about 1% of an antifoaming agent, and an organic solvent or mixture of organic solvents.

DETAILED DESCRIPTION OF THE INVENTION

The herbicidal emulsifiable concentrate compositions of this invention comprise, on a weight to weight basis, about 15% to 40% of a dinitroaniline herbicide, about 1% to 10% of an oxyacetamide herbicide, about 0.01% to 1% phosphoric acid, up to about 30% of an emulsifier or mixture of emulsifiers, up to about 1% of an antifoaming agent, and an organic solvent or mixture of organic solvents.

Preferred herbicidal emulsifiable concentrate compositions of the present invention are those comprising, on a weight to weight basis, about 15% to 40% of a dinitroaniline herbicide, about 1% to 10% of an oxyacetamide herbicide, about 0.01% to 1% phosphoric acid, about 2% to 10% of an alkylarylsufonate, about 0.5% to 5% of a polyalkylene glycol ether, about 1% to 5% of an ethoxylated fatty alcohol, up to about 1% of an antifoaming agent, and an aromatic hydrocarbon solvent having a distillation range of about 135° C. to 305° C.

More preferred emulsifiable concentrate compositions of this invention are those comprising, on a weight to weight basis, about 25% to 35% pendimethalin, about 4% to 8% fluthiamid, about 0.05% to 0.2% phosphoric acid, about 2% to 6% of a dodecylbenzenesulfonate, about 1% to 3% of an alkyl capped ethylene oxide/propylene oxide block copolymer, about 1% to 5% of an ethoxylated $C_{10}$–$C_{16}$ fatty alcohol having about 8 to 12 moles of ethylene oxide per mole, up to about 1% of an antifoaming agent, and an aromatic hydrocarbon solvent having a distillation range of about 135° to 305° C.

Phosphoric acid is an especially important element of the present compositions because it has been found that oxyacetamide herbicides are more stable in the phosphoric acid containing emulsifiable concentrate compositions of the present invention than in corresponding emulsifiable concentrate compositions which do not contain phosphoric acid. In a preferred embodiment of the present invention, the ratio of the oxyacetamide herbicide to the phosphoric acid, on a weight basis, is preferably about 30:1 to 100:1, and more preferably, is about 40:1 to 70:1.

Dinitroaniline herbicides suitable for use in the compositions of this invention have the structural formula I

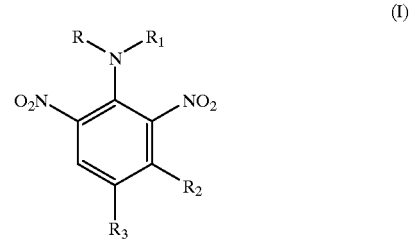

(I)

wherein

R is hydrogen, $C_2$–$C_4$ alkyl or chloroethyl;

$R_1$ is $C_2$–$C_5$ alkyl, chloroethyl, 2-methallyl or cyclopropylmethyl;

$R_2$ is hydrogen, methyl or amino; and $R_3$ is trifluoromethyl, $C_1$–$C_3$ alkyl, $SO_2NH_2$ or $SO_2CH_3$.

Preferred dinitroaniline herbicides for use in this invention include pendimethalin and trifluralin with pendimethalin being more preferred.

Oxyacetamide herbicides suitable for use in the compositions of the present invention are those described in U.S. Pat. Nos. 4,408,055; 4,509,971; 4,540,430; 4,549,899; 4,585,471; 4,645,525; 4,756,741; 4,784,682; 4,788,291; 4,833,243; 4,968,342; 4,988,380; 5,090,991 and 5,234,896; EP Application Nos. 300344-A and 500934-A1; and WO 97/08160.

Preferred oxyacetamide herbicides for use in the compositions of this invention have the structural formula II

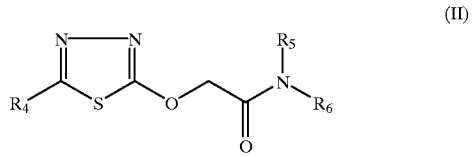

(II)

wherein $R_4$ is hydrogen, F, Cl, Br, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylsulfonyl or $C_1$–$C_4$ haloalkylsulfonyl;

$R_5$ is hydrogen or $C_1$–$C_6$ alkyl; and $R_6$ is phenyl optionally substituted with any combination of from one to three F, Cl, Br, CN, $NO_2$, $C_1$–$C_4$ alkyl, $C_1$–$C_4$ haloalkyl, $C_1$–$C_4$ alkoxy or $C_1$–$C_4$ haloalkoxy groups.

More preferred oxyacetamide herbicides for use in the emulsifiable concentrate compositions of this invention are those wherein $R_4$ is $C_1$–$C_4$ haloalkyl;

$R_5$ is $C_1$–$C_4$ alkyl; and $R_6$ is phenyl optionally substituted with any combination of one or two F, Cl or $C_1$–$C_4$ alkyl groups.

Most preferred oxyacetamide herbicides are those of formula II wherein $R_4$ is $CF_3$, $CHF_2$ or $CFCl_2$;

$R_5$ is isopropyl; and $R_6$ is selected from the group consisting of phenyl, 3-chlorophenyl, 4-chlorophenyl, 2-fluorophenyl, 4-fluorophenyl, 2-methylphenyl, 3-methylphenyl, 4-methylphenyl and 3,4-dimethylphenyl.

An oxyacetamide herbicide which is especially suitable for use in the compositions of this invention is 4'-fluoro-N-isopropyl-2-{[5-(trifluoromethyl)-1,3,4-thiadiazol-2-yl]oxy}acetanilide (fluthiamid).

Emulsifiers suitable for use in the compositions of the present invention include, but are not limited to, alkylarylsulfonates including $C_8$–$C_{18}$ alkylbenzenesulfonates such as calcium dodecylbenzenesulfonate; polyalkylene glycol ethers including alkyl capped ethylene oxide/propylene oxide block copolymers such as butyl capped ethylene oxide/propylene oxide block copolymers; and ethoxylated fatty alcohols including ethoxylated $C_{10}$–$C_{16}$ fatty alcohols having about 8 to 12 moles of ethylene oxide per mole; and mixtures thereof. Preferred emulsifiers include the alkali metal or alkaline earth metal salts of dodecylbenzene sulfonic acid, such as calcium dodecylbenzenesulfonate including SOPROPHOR® 70 a 60% calcium dodecylbenzene sulfonate solution in isobutanol commercially available from Rhodia, Milan, Italy; butyl capped ethylene oxide/propylene oxide block copolymers including WITCONOL® NS 500K a butyl capped ethylene oxide/propylene oxide block copolymer commerically available from Witco SA, Saint-Pierre Les Elbeuf, France; and ethoxylated $C_{10}$–$C_{16}$ fatty alcohols having about 8 to 12 moles of ethylene oxide per mole including RHODASURF® 870 a $C_{13}$ ethoxylated fatty alcohol containing 10 moles of ethylene oxide per mole commercially available from Rhodia, Milan, Italy; and mixtures thereof.

Organic solvents suitable for use in the compositions of this invention include aromatic hydrocarbon solvents such as toluene, xylenes, polynuclear aromatic hydrocarbons such as naphthalenes and alkylnaphthalenes and mixtures thereof, many of which are available from the fractionation of crude oil and in general have distillation ranges in the temperature range of about 135° C. to 305° C., with those having a distillation range of from about 183° C. to 290° C. being most preferred. These solvents are commercially available under a variety of tradenames, e.g. SOLVESSO®200 and AROMATIC®200 both commercially available from Exxon, Fareham, Hants, United Kingdom.

Antifoaming agents suitable for use in the compositions of the present invention include conventional antifoaming agents, with silicone based antifoaming agents such as those sold under the SILCOLAPSE® tradename commercially available from Rhodia, Lyon, France being preferred. In a preferred embodiment of this invention, an antifoaming agent is used at a level sufficient to prevent undesirable foaming during the preparation of tank mixes using the emulsion concentrates of the present invention. Typically, less than 1% by weight of a defoamer is sufficient, with amounts of about 0.01 to about 0.1% by weight being preferred.

The herbicidal emulsifiable concentrate compositions of the present invention may be prepared by admixing all of the ingredients in the organic solvent. In a preferred embodiment of this invention, the compositions are prepared by:

(a) admixing an alkylarylsulfonate, an ethoxylated fatty alcohol, an antifoaming agent and an organic solvent to obtain a first homogeneous mixture;

(b) adding a molten dinitroaniline and a molten polyalkylene glycol ether to the first homogenous mixture of step (a) with stirring to obtain a second homogenous mixture;

(c) adding an oxyacetamide herbicide to the second homogenous mixture of step (b) with stirring to obtain a third homogenous mixture; and (d) adding phosphoric acid to the third homogenous mixture of step (c) with stirring.

The emulsifiable concentrate compositions of this invention are diluted with water and applied as dilute, aqueous emulsions to the locus where weed control is desired. Typical dilution rates are in the range of about 1 L of concentrate per 400 L of water to 4 L of concentrate per 100 L of water. While the compositions of this invention are effective for controlling weeds when employed alone, they may also be used in conjunction with or in combination with other biological chemicals, including other herbicides.

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Preparation of Emulsifiable Concentrate Compositions

A mixture of a 60% calcium dodecylbenzene sulfonate solution in isobutanol commercially available as SOPROPHOR® 70 from Rhodia, Milan, Italy (53.0 g, 5.00% on a weight basis), a $C_{13}$ ethoxylated fatty alcohol containing 10 moles of ethylene oxide per mole commercially available as RHODASURF® 870 from Rhodia, Milan, Italy (32.0 g, 3.00% on a weight basis), a silicone antifoam commercially available as SILCOLAPSE® 431 from Rhodia, Lyon, France (0.1 g, 0.01% on a weight basis), and an aromatic hydrocarbon mixture ($C_{10}$–$C_{13}$)aromatics having a distillation range of about 226–279° C. commercially available as SOLVESSO® 200 from Exxon, Fareham, Hants, United Kingdom (557.0 g, 52.29% on a weight basis) is stirred until homogeneous. Molten pendimethalin (333.3 g, 90% real, 31.33% on a weight basis) and a molten butyl capped ethylene oxide/propylene oxide block copolymer commercially available as WITCONOL® NS 500K from Witco SA, Saint-Pierre Les Elbeuf, France (21.0 g, 2.00% on a weight basis) are added to the mixture with stirring. Solid fluthiamid (66.7 g, 90% real, 6.27% on a weight basis) is then added to the mixture and the mixture is stirred until all of the solids dissolve. An 85% phosphoric acid solution (1.0 g, 0.10% on a weight basis) is added to the mixture, with stirring until homogeneous, to obtain the emulsifiable concentrate composition identified as composition number 1 in Table I.

Using essentially the same procedure, the emulsifiable concentrate compositions identified as composition numbers 2 to 14 in Table I are obtained.

TABLE I

Emulsifiable Concentrate Compositions

Ingredient - % w/w

| Comp. No. | Pendimethalin | Fluthiamid | 85% Phosphoric Acid Solution | SOPROPHOR ® 70 | RHODASURF ® 870 | WITCONOL ® NS 500K | SILCOLAPSE ® 431 | SOLVESSO ® 200 |
|---|---|---|---|---|---|---|---|---|
| 1  | 31.33[1] | 6.27[1] | 0.10 | 5.00 | 3.00 | 2.00 | 0.01 | 52.29 |
| 2  | 28.20[2] | 5.64[2] | 0.10 | 5.00 | 3.00 | 2.00 | 0.01 | 56.05 |
| 3  | 32.00[1] | 6.40[1] | 0.05 | 3.84 | 2.60 | 1.06 | 0.01 | 54.04 |
| 4  | 32.00[1] | 6.40[1] | 0.10 | 3.84 | 2.60 | 1,06 | 0.01 | 53.99 |
| 5  | 32.00[1] | 6.40[1] | 0.15 | 3.84 | 2.60 | 1.06 | 0.01 | 53.94 |
| 6  | 32.00[1] | 6.40[1] | 0.20 | 3.84 | 2.60 | 1.06 | 0.01 | 53.89 |
| 7  | 32.00[1] | 6.40[1] | 0.25 | 3.84 | 2.60 | 1.06 | 0.01 | 53.84 |
| 8  | 32.00[1] | 6.40[1] | 0.50 | 3.84 | 2.60 | 1.06 | 0.01 | 53.59 |
| 9  | 28.80[2] | 5.76[2] | 0.05 | 3.84 | 2.60 | 1.06 | 0.01 | 57.88 |
| 10 | 28.80[2] | 5.76[2] | 0.10 | 3.84 | 2.60 | 1.06 | 0.01 | 57.83 |
| 11 | 28.80[2] | 5.76[2] | 0.15 | 3.84 | 2.60 | 1.06 | 0.01 | 57.78 |
| 12 | 28.80[2] | 5.76[2] | 0.20 | 3.84 | 2.60 | 1.06 | 0.01 | 57.73 |
| 13 | 28.80[2] | 5.76[2] | 0.25 | 3.84 | 2.60 | 1.06 | 0.01 | 57.68 |
| 14 | 28.80[2] | 5.76[2] | 0.50 | 3.84 | 2.60 | 1.06 | 0.01 | 57.43 |

[1] 90% real
[2] 100% real

EXAMPLE 2

Evaluation of Storage Stability of Test Compositions

Samples of test compositions identified in Table I and a comparative composition identified below are placed in glass bottles. The bottles are capped and placed in a temperature controlled storage incubator.

After completing the required storage period, the samples are removed and assayed for pendimethalin and fluthiamid content. The active ingredient content is expressed as a percentage relative to the active ingredient content prior to storage (% Initial Content). The results are summarized in Table II.

TABLE II

Evaluation of Storage Stability

| Composition Number | Storage Temperature (° C.) | Storage Period (weeks) | 85% Phosphoric Acid Solution (% w/w) | % Initial Content Pendimethalin | Fluthiamid |
|---|---|---|---|---|---|
| Comparative Composition | 54 | 2 | 0 | 100 | 95 |
| 3 | 54 | 2 | 0.05 | 100 | 100 |
| 4 | 54 | 2 | 0.10 | 100 | 99 |
| 5 | 54 | 2 | 0.15 | 101 | 99 |
| 6 | 54 | 2 | 0.20 | 100 | 98 |
| 6 | 37 | 12 | 0.20 | 99 | 98 |
| 7 | 54 | 2 | 0.25 | 103 | 103 |
| 8 | 54 | 2 | 0.50 | 102 | 102 |
| Comparative Composition | 37 | 12 | 0 | 101 | 94 |
| 3 | 37 | 12 | 0.05 | 100 | 99 |
| 4 | 37 | 12 | 0.10 | 99 | 101 |
| 5 | 37 | 12 | 0.15 | 99 | 99 |
| 6 | 37 | 12 | 0.20 | 99 | 98 |

As can be seen from the data in Table II, fluthiamid is more stable in the emulsifiable concentrate compositions of the present invention which contain phosphoric acid than the comparative emulsifiable concentrate composition which does not contain phosphoric acid.

COMPARATIVE COMPOSITION[1]

| Ingredient | % w/w |
|---|---|
| Pendimethalin (90% real) | 32.00 |
| Fluthiamid (90% real) | 6.40 |
| SOPROPHOR ® 70 | 3.84 |
| RHODASURF ® 870 | 2.60 |
| WITCONOL ® NS 500K | 1.06 |
| SILCOLAPSE ® 431 | 0.01 |
| SOLVESSO ® 200 | 54.09 |

[1] Prepared according to the procedure described in Example 1 except that the 85% phosphoric acid solution is not added.

What is claimed is:

1. A herbicidal emulsifiable concentrate composition which comprises, on a weight to weight basis, about 15% to 40% of a dinitroaniline herbicide, about 1% to 10% of an oxyacetamide herbicide, about 0.01% to 1% phosphoric acid, up to about 30% of an emulsifier or mixture of emulsifiers, up to about 1% of an antifoaming agent, and an organic solvent or mixture of organic solvents.

2. The composition according to claim 1 wherein the emulsifier or mixture of emulsifiers comprises about 2% to 10% of an alkylarylsulfonate, about 0.5% to 5% of a polyalkylene glycol ether and about 1% to 5% of an ethoxylated fatty alcohol, and the organic solvent or mixture of organic solvents is an aromatic hydrocarbon solvent having a distillation range of about 135° C. to 305° C.

3. The composition according to claim 1 which comprises, on a weight to weight basis, about 25% to 35% pendimethalin, about 4% to 8% fluthiamid, about 0.05% to 0.2% phosphoric acid, about 2% to 6% of a dodecylbenzenesulfonate, about 1% to 3% of an alkyl capped ethylene oxide/propylene oxide block copolymer, about 1% to 5% of an ethoxylated $C_{10}$–$C_{16}$ fatty alcohol having about 8 to 12 moles of ethylene oxide per mole, up to about 1% of an antifoaming agent, and an aromatic hydrocarbon solvent having a distillation range of about 135° C. to 305° C.

4. The composition according to claim 1 wherein the ratio of the oxyacetamide herbicide to the phosphoric acid on a weight basis is about 30:1 to 100:1.

5. The composition according to claim 4 wherein the ratio is about 40:1 to 70:1.

6. The composition according to claim 1 wherein the emulsifier is selected from the group consisting of an alkylarylsufonate, a polyalkylene glycol ether, and an ethoxylated fatty alcohol, and mixtures thereof.

7. The composition according to claim 6 wherein the alkylarylsulfonate is a $C_8$–$C_{18}$ alkylbenzenesulfonate; the polyalkylene glycol ether is an alkyl capped ethylene oxide/propylene oxide block copolymer, and the ethoxylated fatty alcohol is an ethoxylated $C_{10}$–$C_{16}$ fatty alcohol having about 8 to 12 moles of ethylene oxide per mole.

8. The composition according to claim 1 wherein the antifoaming agent is present.

9. The composition according to claim 1 wherein the dinitroaniline herbicide has the structural formula I

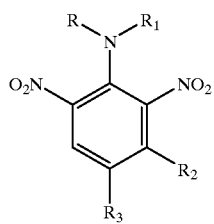

(I)

wherein

R is hydrogen, $C_2$–$C_4$ alkyl or chloroethyl;

$R_1$ is $C_2$–$C_5$ alkyl, chloroethyl, 2-methallyl or cyclopropylmethyl;

$R_2$ is hydrogen, methyl or amino; and $R_3$ is trifluoromethyl, $C_1$–$C_3$ alkyl, $SO_2NH_2$ or $SO_2CH_3$.

10. The composition according to claim 1 wherein the dinitroaniline herbicide is selected from the group consisting of pendimethalin and trifluralin.

11. The composition according to claim 1 wherein the dinitroaniline herbicide is pendimethalin.

12. The composition according to claim 1 wherein the oxyacetamide herbicide has the structural formula II

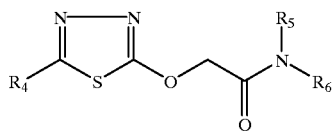

(II)

wherein $R_4$ is hydrogen, F, Cl, Br, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylsulfonyl or $C_1$–$C_4$ haloalkylsulfonyl;

$R_5$ is hydrogen or $C_1$–$C_6$ alkyl; and $R_6$ is phenyl optionally substituted with any combination of from one to three F, Cl, Br, CN, $NO_2$, $C_1$–$C_4$ alkyl, $C_1$–$C_4$ haloalkyl, $C_1$–$C_4$ alkoxy or $C_1$–$C_4$ haloalkoxy groups.

13. The composition according to claim 12 wherein $R_4$ is $C_1$–$C_4$ haloalkyl;

$R_5$ is $C_1$–$C_4$ alkyl; and $R_6$ is phenyl optionally substituted with any combination of one or two F, Cl or $C_1$–$C_4$ alkyl groups.

14. The composition according to claim 13 wherein $R_4$ is $CF_3$, $CHF_2$ or $CFCl_2$;

$R_5$ is isopropyl; and $R_6$ is selected from the group consisting of phenyl, 3-chlorophenyl, 4-chlorophenyl, 2-fluorophenyl, 4-fluorophenyl, 2-methylphenyl, 3-methylphenyl, 4-methylphenyl and 3,4-dimethylphenyl.

15. The composition according to claim 1 wherein the oxyacetamide herbicide is fluthiamid.

16. The composition according to claim 1 wherein the organic solvent is an aromatic hydrocarbon solvent having a distillation range of about 135° C. to 305° C.

17. The composition according to claim 16 wherein the distillation range is about 183° C. to 290° C.

18. An aqueous tank mixture which comprises water and a composition as described in claim 1.

19. A method for the control of undesirable plants which comprises applying to the locus of the undesirable plants an aqueous tank mixture comprising water and a composition as described in claim 1.

* * * * *